United States Patent [19]

Meybeck et al.

[11] Patent Number: 5,653,983
[45] Date of Patent: Aug. 5, 1997

[54] **COMPOSITIONS FOR THE PIGMENTATION OF THE SKIN OR OF THE HAIR CONTAINING AN EXTRACT OF *MARRUBIUM VULGARE*, THE PROCESS FOR ITS MANUFACTURE AND ITS APPLICATION**

[75] Inventors: Alain Meybeck; Frédéric Bonte, both of Courbevoie; Marc Dumas, Colombes, all of France

[73] Assignee: LVMH Recherche, Colombes Cedex, France

[21] Appl. No.: 468,419

[22] Filed: Jun. 6, 1995

Related U.S. Application Data

[63] Continuation of Ser. No. 185,938, Jan. 19, 1994, abandoned.

[30] Foreign Application Priority Data

Jul. 19, 1991 [FR] France .................. 91 09198

[51] Int. Cl.⁶ .................. A61K 35/78; A61K 7/06
[52] U.S. Cl. .................. 424/195.1; 424/70.6; 424/401; 514/783; 514/844
[58] Field of Search .................. 424/195.1, 62, 424/401, 420, 70.6, 63; 514/783, 844, 880

[56] References Cited

U.S. PATENT DOCUMENTS

| | | | |
|---|---|---|---|
| 5,034,228 | 7/1991 | Meybeck et al. | 424/401 |
| 5,164,182 | 11/1992 | Meybeck et al. | 424/195.1 |
| 5,198,225 | 3/1993 | Meybeck et al. | 424/450 |
| 5,279,834 | 1/1994 | Meybeck | 424/450 |
| 5,290,562 | 3/1994 | Meybeck et al. | 424/450 |

FOREIGN PATENT DOCUMENTS 1098065  1/1968  United Kingdom.

OTHER PUBLICATIONS

Aliev et al. *Uchenye Zapiski Azerbaidzhan Gosudarst Univ Im S.M Kirova*, vol. 9, pp. 69–75, (1956) (abstract only).
Kchour et al. *Arch Inst Pasteur Tunis*, vol. 40, p. 129, (1963) (Abstract Only).
Bartarelli. *Boll Chim Farm*, vol. 105(11), pp. 787–798, (1966) (Abstract Only).
Rizzo. *Rev Sudamericana Endocrinol Immunol Quimoterap*, vol. 16, p. 743, (1933) (Abstract Only).
Cath. Thesis—Univ Marsaille (1933) (Abstract Only).
Johsi et al. *Biochemical and Biophysical Research Communications*, vol. 142(1), pp. 265–274, (1987).
U.S Dispensary 23rd Edition, Wood et al., p. 1435, (1943).
"Extracts of Plants", Manufacturing Chemist and Aerosol News vol. 53, No. 7, Jul. 1982.
Chemical Abstracts vol. 86, No. 1, No. 2355U, Karryev et al.
Chemical Abstracts vol. 91, No. 15, No. 120333m, Nilov et al.

*Primary Examiner*—John Kight
*Assistant Examiner*—Howard C. Lee
*Attorney, Agent, or Firm*—Watson Cole Stevens Davis, P.L.L.C.

[57] ABSTRACT

The invention relates to the use of an extract of Marrubium vulgare for the preparation of a cosmetic or a pharmaceutical composition, especially dermatological composition, intended in particular for promoting the pigmentation of the skin, preventing or slowing down the appearance of white hair and treating pigmentation disorders.

35 Claims, No Drawings

COMPOSITIONS FOR THE PIGMENTATION OF THE SKIN OR OF THE HAIR CONTAINING AN EXTRACT OF *MARRUBIUM VULGARE*, THE PROCESS FOR ITS MANUFACTURE AND ITS APPLICATION

This application is a continuation of application Ser. No. 08/185,938, filed Jan. 19, 1994, now abandoned.

The present invention relates essentially to a cosmetic or pharmaceutical composition, especially dermatological composition, containing an extract of Marrubium vulgare, intended in particular for promoting the pigmentation of the skin or hair, and to the process for its manufacture.

The present invention further relates to the use of an extract of Marrubium vulgare for the preparation of such a cosmetic or pharmaceutical composition intended in particular for treating pigmentation disorders.

The various species of the genus Marrubium vulgare belong to the family of the Labiatae. Marrubium vulgare, also called white horehound, is commonly found in uncultivated locations, especially in Mediterranean regions and also in West Asia and North Africa.

According to tradition, the leaves and flowering tops of this plant possess expectorant and fluidifying properties towards bronchial secretions. It is also said to have an effect on extrasystolic arrhythmia (see, in particular, Précis de Matière Médicale (Precis of Medical Topics) by R. R. PARIS and Mme H. MOYSE, volume III, published by MASSON et Compagnie, 1971, page 293).

The present invention is based on the discovery that extracts of Marrubium vulgare, in particular those originating from the aerial parts and especially from the stems and leaves, have valuable biological properties which can be utilized in the cosmetic and pharmaceutical fields. In particular, the inventors have observed that these extracts unexpectedly possess a melanogenesis-stimulating activity on the melanocytes present in the skin or the hair follicles, especially those on the scalp, and thus make it possible to promote the pigmentation of the skin or hair as well as to treat pigmentation disorders of the skin and hair, more particularly by promoting the biosynthesis of melanin. Very good results in this field have been obtained with extracts of the aerial parts of Marrubium vulgare, in particular the stems and leaves.

One object of the present invention is therefore to solve the new technical problem which consists in providing a novel cosmetic or pharmaceutical composition, especially dermatological composition, intended in particular for promoting the pigmentation of the skin and preventing or slowing down the appearance of white hair.

A further object of the present invention is to solve the new technical problem which consists in preparing a novel formulation of a cosmetic or pharmaceutical composition having a good melanogenesis-stimulating activity on the melanocytes present in the skin or the hair follicles, especially those on the scalp.

A further object of the present invention is to provide a solution to the new technical problem which consists in providing a particularly easily obtainable plant extract which in itself has a good melanogenesis-stimulating activity on the melanocytes present in the skin or the hair follicles, without having to isolate an active substance of any kind, these isolation processes generally being lengthy and expensive.

All these new technical problems are solved for the first time by the present invention in a satisfactory manner which can be used on the industrial scale.

Thus, according to a first feature, the present invention relates to a cosmetic or pharmaceutical composition, especially dermatological composition, intended in particular for promoting the pigmentation of the skin and preventing or slowing down the appearance of white hair, said composition comprising, as the active ingredient, a cosmetically or pharmaceutically effective amount of an extract of Marrubium vulgare, if appropriate in a cosmetically or pharmaceutically acceptable excipient.

In the present description and the claims, "cosmetically or pharmaceutically effective amount" is understood as meaning an amount at least equal to the minimum amount which is necessary for observing a significant cosmetic or pharmaceutical effect.

According to one particular characteristic of the invention, the extract of Marrubium vulgare is an extract of the aerial parts, in particular the stems and leaves.

According to another characteristic, the above-mentioned extract of Marrubium vulgare is an organic extract, in particular of the aerial parts such as the stems and leaves, which is advantageously obtained by a process comprising at least one extraction step, for example with a solvent selected from the group consisting of water, alcohols preferably containing from 1 to 4 carbon atoms, such as methanol, ethanol or propanol, an aqueous-alcoholic mixture of these alcohols, chlorinated solvents containing 1 or 2 carbon atoms, such as chloroform or dichloromethane, and organic esters preferably containing 3 to 6 carbon atoms, such as ethyl acetate. More generally, other solvents which can be used are organic solvents such as aromatic hydrocarbons, especially benzene, toluene or xylene, halogenated aliphatic or aromatic hydrocarbons, dialkyl ethers, dialkyl ketones, alkanols, carboxylic acids and esters thereof, or other solvents such as dimethylformamide, dioxane, tetrahydrofuran and dimethyl sulfoxide. The ratio of plant material to extraction agent is not critical but is generally between 1:5 and 1:20 parts by weight, preferably about 1:10. The extraction is carried out at temperatures between room temperature and the boiling point of the solvent used for the extraction. A valuable extraction technique is the so-called Soxhlet extraction technique.

However, it is also possible simply to carry out the extraction under reflux at normal atmospheric pressure for 2 to 4 h, if appropriate after the plant material has been left to macerate for 2 to 4 h in the cold extraction solvent.

When the extraction is complete, the phase containing the extract is filtered and then concentrated and/or evaporated to dryness under reduced pressure or by lyophilization.

This gives an extract according to the invention.

In general, the concentration of the extracts used according to the present invention for the preparation of a cosmetic or pharmaceutical composition, expressed by dry weight, is between 0.0001% and 5% by weight, preferably between 0.01% and 0.5% by weight, based on the total weight of the composition.

The cosmetic or pharmaceutical compositions, especially dermatological compositions, according to the present invention can be prepared in forms suitable for various modes of administration. In particular, they can be presented in a form intended for surface administration to the skin or scalp, such as a cream, a gel, a milk or a lotion, in order to promote the pigmentation of the skin and prevent or slow down the appearance of white hair.

Thus the cosmetic or pharmaceutical compositions, especially dermatological compositions, according to the invention have various applications in cosmetology or pharmacy, especially in dermatology, in particular when it is desired to restore normal pigmentation or increase this pigmentation.

For example, these compositions can be used as sun products for accelerating or intensifying tanning, which, in addition to the aesthetic advantage often sought after, makes it possible to strengthen the natural defenses against ultraviolet radiation by increasing the proportion of melanin in the epidermis. These compositions can also be used in the form of creams, for example, in order to give the skin a more sunburnt appearance, or else in the form of lotions in order to prevent or slow down the appearance of white hair. Furthermore, in dermatology, the compositions according to the present invention can be used as therapeutic agents, either by themselves or in association with other medicaments, in particular by topical administration in the treatment of dysfunctions of the melanocytes.

Advantageously, the cosmetic or pharmaceutical compositions according to the invention which are intended for topical administration contain at least one agent for promoting penetration and diffusion in the cutaneous structures in question, such as the agents commonly used in the fields of cosmetology and dermopharmacy, for example glycerol, propylene glycol, oleic acid or essential oils, especially menthol and eucalyptol.

In one advantageous embodiment, a cosmetic or pharmaceutical composition according to the invention also contains a xanthine, in particular 1-methylxanthine, 3-methylxanthine, 3-isobutylmethylxanthine or theophylline, preferably at a concentration by weight of between 0.001% and 2% and particularly preferably of between 0.01% and 0.5%, based on the total weight of the composition.

In another embodiment, applicable in particular within the framework of activating the pigmentation of the skin or hair, a cosmetic or pharmaceutical composition according to the invention also contains tyrosine or a derivative thereof, such as glucose tyrosinate or N-malyltyrosine, preferably at a concentration by weight of between 0.001% and 10%, based on the total weight of the composition.

In yet another embodiment, applicable in particular within the framework of activating the pigmentation of the hair, a cosmetic or pharmaceutical composition according to the invention also contains an effective concentration of at least one other active substance selected from vitamins, in particular the B vitamins, quinine or derivatives thereof, rubefacients such as methyl nicotinate, a papilla fibroblast culture supernatant as defined in the document EP-A-272 920, keratin hydrolyzates, trace elements such as zinc, selenium and copper, 5-α-reductase inhibitors such as progesterone, cyproterone acetate and minoxidil, azelaic acid and derivatives thereof, a 1,4-dimethyl-4-azasteroid, in particular 17-β-N,N-diethylcarbamoyl-4-methyl-4-aza-5-α-androstan-3-one, or else an extract of Serenoa repens.

In yet another embodiment, a cosmetic or pharmaceutical composition according to the invention also contains hydrated lipidic lamellar phases or liposomes, which may or may not incorporate the extract of Marrubium vulgare defined above.

According to a second feature, the present invention further relates to a process for the manufacture of a cosmetic or pharmaceutical composition, especially dermatological composition, intended in particular for promoting the pigmentation of the skin, preventing or slowing down the appearance of white hair and treating pigmentation disorders of the skin or hair, said process comprising the incorporation of at least one extract of Marrubium vulgare, as defined above, into a cosmetically or pharmaceutically acceptable excipient, vehicle or carrier.

According to a third feature, the invention relates to the use of an extract of Marrubium vulgare, as defined above, for the preparation of a cosmetic or pharmaceutical composition, especially dermatological composition, intended in particular for promoting the pigmentation of the skin, preventing or slowing down the appearance of white hair or treating pigmentation disorders of the skin or hair.

According to yet another feature, the present invention further relates to a cosmetic or therapeutic method of treating a pigmentation insufficiency or pigmentation disorders, said method comprising the application of an effective amount of at least one extract of Marrubium vulgare, as defined above, advantageously incorporated in a cosmetically or pharmaceutically acceptable excipient, vehicle or carrier, preferably to the affected areas of the skin or scalp of a human being, in order to restore normal pigmentation of the skin or hair and/or increase this pigmentation.

In all the foregoing features, the extract of Marrubium vulgare, as defined above, can be used in the presence of hydrated lipidic lamellar phases or liposomes, which may or may not incorporate said extract. It is pointed out that the expression "incorporate" covers the case where the extract is totally incorporated and the case where only a certain amount of this extract is incorporated in the hydrated lipidic lamellar phases or the liposomes.

The term "lipidic" in the expression "lipidic lamellar phase" covers all substances which comprise a so-called fatty hydrocarbon chain generally containing more than 5 carbon atoms, this substance usually being called a "lipid".

According to the invention, the lipids used to form the lipidic lamellar phases or the liposomes are amphiphilic lipids, i.e. lipids consisting of molecules which possess either an ionic or a non-ionic hydrophilic group and a lipophilic group, these amphiphilic lipids being capable of forming lipidic lamellar phases or liposomes in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an egg or soya lecithin, a phosphatidylserine, a sphyngomyelin, a cerebroside or an oxyethylenated polyglycerol stearate.

It is preferable according to the invention to use a mixture of lipids made up of at least one amphiphilic lipid and at least one hydrophobic lipid such as a sterol like cholesterol or β-sitosterol. The amount of hydrophobic lipid, expressed in mol, must not generally exceed the amount of amphiphilic lipid and preferably must not exceed 0.5 times this amount.

The compounds or the extracts containing these compounds used according to the present invention can be incorporated into hydrated lipidic lamellar phases or into liposomes by known preparative techniques described for example in the document EP-B1-0 087 993 =U.S. Pat. No. 4,508,703, if appropriate in combination with the document EP-B1-0 107 559 = U.S. Pat. No. 4,621,023.

Other objects, characteristics and advantages of the invention will become clearly apparent from the following explanatory description referring to several Examples, which are given simply by way of illustration.

In fact, the present invention is in no way limited to the embodiments described and illustrated. Thus, for example, it also covers a cosmetic or dermatological composition intended for preventing the eyebrows or eyelashes from turning white or for slowing down this process.

The percentages are given by weight in the Examples, unless indicated otherwise.

EXAMPLE 1

Preparation of a methanolic extract of Marrubium vulgare 500 g of aerial parts of Marrubium vulgare, composed of stems and leaves, are refluxed for 3 h with about 5 l of methanol.

The methanolic extracts are filtered and the filtrate is evaporated under reduced pressure and then lyophilized to give a methanolic extract of Marrubium vulgare called extract $I_1$.

EXAMPLE 2

Preparation of an ethyl acetate extract of Marrubium vulgare

An ethyl acetate extract of Marrubium vulgare called extract $I_2$ is obtained by following the procedure described in Example 1, except that the whole plant is used and ethyl acetate is used as the solvent.

EXAMPLE 3

Incorporation of an extract of aerial parts of Marrubium vulgare into hydrated lipidic lamellar phases or into liposomes An extract of aerial parts of Marrubium vulgare obtained according to Example 1 is incorporated into hydrated lipidic lamellar phases or into liposomes by the following preparative technique:

The following are weighed out:

soya lecithin: 1.8 g

β-sitosterol: 0.2 g lyophilized extract of Marrubium vulgare $I_1$ of Example 1: 0.03 g These constituents are dissolved in a mixture made up of 25 ml of dichloromethane and 10 ml of methanol.

The resulting mixture is evaporated on a rotary evaporator at a temperature of 60° C. under reduced pressure.

The resulting lipidic film is then taken up and dispersed in distilled water qsp 50 g at room temperature for 12 h, with agitation.

The suspension of lipidic vesicles obtained is then homogenized by treatment with ultrasound for 10 min at 4° C., at a power of 150 W.

The resulting liposomes have a mean size of about 140 nm.

In one advantageous variant, this suspension is then gelled by being mixed with 50 g of 1.25% Carbopol® 940 gel, separately prepared in conventional manner. This gives about 100 g of a gelled suspension of liposomes encapsulating the extract of Marrubium vulgare, the concentration of which is about 0.030%, based on the total weight of the suspension.

This gel is called "composition $I_3$" and can be used as such within the framework of the invention.

EXAMPLE 4

Measurement of the efficacy of an extract of Marrubium vulgare according to the invention on melanocytes in culture Protocol:

S91 murine melanocytes, inoculated at a rate of $2 \cdot 10^5$ cells per dish, are cultivated in EMEM complemented with non-essential amino acids and also containing 1% of fetal calf serum and 0.08 µg/ml of mitomycin C. 24 h after inoculation, the culture medium is replaced with fresh medium free of mitomycin C and comprising only complemented EMEM, 1% of fetal calf serum and, if appropriate, the test product solubilized in DMSO.

Six days after inoculation, the cells are removed and isolated by centrifugation and the cellular residue is recovered and dissolved in 0.5N sodium hydroxide.

The optical density of the solution obtained is read on a spectrophotometer at 405 nm, which makes it possible to evaluate the amount of melanin formed by comparison with the optical density of a solution of melanin of known concentration.

The cells are also counted and the amount of melanin formed per $10^6$ cells is calculated.

Extracts $I_1$ and $I_2$ of Marrubium vulgare were tested, at various concentrations, using as positive control a culture receiving only β-MSH (melanocyte-stimulating hormone) at a concentration of $2 \cdot 10^{-8}$M.

The melanogenesis-stimulating efficacy E of the test products is calculated by means of the following formula:

$$E = \frac{q_p - q_o}{q_t - q_o} \times 100$$

in which the quantities q represent the amounts of melanin formed per $10^6$ cells:

$q_p$: culture receiving the test product $q_t$: culture receiving β-MSH $q_o$: control culture receiving no product The efficacy E of the extracts tested at different concentrations, calculated according to the above formula, is shown a) in Table I below for extract $I_1$ of Example 1, or b) in Table II below for extract $I_2$ of Example 2.

The tests were performed with three dishes per concentration and per product, so the values shown in Tables I and II, relating to the number of cells per dish and to the amount of melanin, are mean values.

A statistical study by the Student t test compares the results of the control cultures with those of the cultures treated with the products according to the invention or with β-MSH.

S = significant at 5%,

NS = not significant at 5%.

TABLE I

Test with extract $I_1$, of Marrubium vulgare

| Concentration of extract $I_1$ (µg/ml) | Number of cells ± standard deviation per dish × $10^{-3}$ | Melanin, µg per $10^6$ cells | Efficacy E | t |
|---|---|---|---|---|
| (Control) 0 | 167 ± 0 | 58 ± 4 | 0 | |
| (Positive control, β-MSH) 0 | 161 ± 5 | 156 ± 11 | 100 | S |
| 1 | 171 ± 7 | 61 ± 1 | +3 | NS |
| 2.5 | 169 ± 4 | 66 ± 2 | +8 | NS |
| 10 | 156 ± 6 | 88 ± 5 | +31 | S |

TABLE II

Test with extract I$_2$ of *Marrubium vulgare*

| Concentration of extract I$_2$ (μg/ml) | Number of cells ± standard deviation per dish × 10$^{-3}$ | Melanin, μg per 10$^6$ cells | Efficacy E | t |
|---|---|---|---|---|
| Control | 173 ± 3 | 62 ± 1 | 0 | |
| Control, β-MSH | 152 ± 13 | 158 ± 10 | 100 | S |
| 1 | 171 ± 7 | 73 ± 4 | +12 | S |
| 2.5 | 166 ± 12 | 80 ± 2 | +19 | S |
| 5 | 157 ± 1 | 87 ± 12 | +27 | S |

Tables I and II above show that the extracts according to the invention stimulate the production of melanin to a significant extent, representing a totally unexpected result for those skilled in the art.

Various Examples of the formulation of cosmetic or pharmaceutical compositions, especially dermatological compositions, are given below.

EXAMPLE 5

Lotion for Promoting the Pigmentation of the Hair

| | |
|---|---|
| extract I$_1$ | 0.15 g |
| propylene glycol | 5 g |
| Crémophor RH40 ® | 1 g |
| ethanol | 30 g |
| perfumed aqueous excipient qsp | 100 g |

Apply the lotion to the hair at a rate of 1 ml twice a day for 6 months to obtain a significant pigmenting effect.

EXAMPLE 6

Gel for Promoting Tanning

The gel is prepared from the following two phases A and B:

| 1) Phase A | |
|---|---|
| extract I$_1$ | 0.1 g |
| malyltyrosine | 2 g |
| propylene glycol | 4 g |
| glycerol | 0.5 g |
| Crémophor RH40 ® | 1 g |
| ethanol | 25 g |
| perfumed aqueous excipient qsp | 50 g |
| 2) Phase B | |
| 1.25% Carbopol 940 ® gel | 50 g |

Phase A is added gradually to phase B and the components are mixed with a propeller mixer until dispersion is complete.

This gives a gel for promoting tanning of the skin, which can be applied before or during exposure to the sun.

What is claimed is:

1. A cosmetic or pharmaceutical composition, formulated for a topical application to the skin or scalp, comprising, as active ingredient, a cosmetically or pharmaceutically effective amount of an extract of Marrubium vulgare obtained by extraction with a polar solvent in a topically acceptable excipient selected from the group consisting of a cream, a gel, a milk, and a lotion.

2. The composition according to claim 1, wherein said extract of Marrubium vulgare is an organic extract of the aerial parts.

3. The composition of claim 1, wherein the extract of Marrubium vulgare is an organic extract obtained by a process comprising at least one extraction step of Marrubium vulgare comprising the aerial parts with a solvent selected from the group consisting of water, alcohols, an aqueous-alcoholic mixture with at least one of these alcohols, chlorinated solvents containing 1 or 2 carbon atoms and organic esters.

4. The composition of claim 1, wherein the concentration of the extract of Marrubium vulgare, expressed by dry weight, ranges between 0.001% and 5%, based on the total weight of the composition.

5. The composition of claim 1, wherein the concentration of the extract of Marrubium vulgare, expressed by dry weight, ranges between 0.01% and 0.5%, based on the total weight of the composition.

6. The composition of claim 1, further comprising a xanthine at a concentration ranging between 0.0001% and 2% by weight, based on the total weight of the composition.

7. The composition of claim 1, further comprising a xanthine at a concentration ranging between 0.01% and 0.5% by weight, based on the total weight of the composition.

8. The composition of claim 1, further comprising tyrosine or a derivative thereof at a concentration ranging between 0.001% and 10% by weight, based on the total weight of the composition.

9. The composition of claim 1, further comprising an effective concentration of at least one other active substance for activating pigmentation of the hair selected from vitamins, quinine, rubefacients, a papilla fibroblast culture supernatant, keratine hydrolyzates, trace elements, 5-α-reductase inhibitors, azelaic acid, a 1,4 dimethyl-4-azasteroid and an extract of Serenoa repens.

10. The composition of claim 1, in a form selected from the group consisting of a cream, a gel, a milk and a lotion.

11. The composition of claim 1, wherein the aerial parts are selected from the stems and leaves.

12. The composition of claim 7, wherein said xanthine is selected from the group consisting of 1-methylxanthine, 3-methylxanthine, 3-isobutylmethylxanthine and theophylline.

13. The composition of claim 8, wherein said tyrosine is selected from the group consisting of glucose tyrosinate and N-malyltyrosine.

14. The composition of claim 9, wherein said vitamin is a B vitamin; said rubefacient is methyl nicotinate, said trace element element is selected from the group consisting of zinc, selenium and copper; said 5-α-reductase inhibitor is selected from the group consisting of progesterone, cyproterone acetate and minoxidil; said 1,4-dimethyl-4-azasteroid is 17-β-N,N-diethylcarbamoyl-4-methyl-4-aza-5-α-androstan-3-one.

15. A cosmetic or pharmaceutical composition, formulated for a topical application to the skin or scalp, comprising, as active ingredient, a cosmetically or pharmaceutically effective amount of an extract of Marrubium vulgare obtained by extraction with a polar solvent in a topically acceptable excipient, wherein the concentration of the extract of Marrubium vulgate, expressed by dry weight, ranges between 0.001% and 5%, based on the total weight of the composition.

16. A cosmetic or pharmaceutical composition, formulated for a topical application to the skin or scalp, comprising:

as active ingredient, a cosmetically or pharmaceutically effective amount of an extract of Marrubium vulgare obtained by extraction with a polar solvent;

an agent for promoting penetration and diffusion of the extract into the skin or scalp; and a topically acceptable excipient.

17. A composition of claim 16, wherein the agent is selected from the group consisting of glycerol, propylene glycol, oleic acid, menthol, and eucalyptol.

18. A cosmetic or pharmaceutical composition, formulated for a topical application to the skin or scalp, comprising, as active ingredient, a cosmetically or pharmaceutically effective mount of an extract of Marrubium vulgare obtained by extraction with a polar solvent in a topically acceptable excipient, wherein the polar solvent is selected from the group consisting of methanol and ethyl acetate.

19. A cosmetic or pharmaceutical composition formulated for topical application to the skin or scalp to stimulate melanogenesis in melanocyte cells, comprising, as active ingredient, a melanogenesis-stimulating extract of Marrubium vulgare obtained by extraction with a polar solvent in an mount effective to promote melanin biosynthesis, and a topically acceptable excipient.

20. A composition of claim 19, wherein the composition further comprises an agent for promoting penetration and diffusion of the extract into the skin or scalp.

21. A composition of claim 20, wherein the agent is selected from the group consisting of glycerol, propylene glycol, oleic acid, menthol, and eucalyptol.

22. A method of treating a pigmentation insufficiency or pigmentating disorders on given areas of the scalp or skin of a human being, comprising applying a natural pigmentating effective amount of an extract of Marrubium vulgare on said areas to restore natural pigmentation of the skin or hair, wherein the extract obtained by extraction with a polar solvent.

23. A method of promoting natural pigmentation of given areas of the skin or hair of a human being, comprising applying on said areas a pigmenting promoting effective amount of an extract of Marrubium vulgare obtained by extraction with a polar solvent.

24. The method of claim 23, wherein said extract of Marrubium vulgare is applied to the hair thereby preventing or slowing down the appearance of white hair.

25. The method of claim 22, wherein said extract of Marrubium vulgare is incorporated in an excipient selected from a cosmetically acceptable excipient and a pharmaceutically acceptable excipient to constitute a composition, to a concentration of an extract of Marrubium vulgare ranging between 0.001% and 5% by weight, based on the total weight of the composition.

26. The method of claim 22, wherein said extract of Marrubium vulgare is an extract of the aerial parts of Marrubium vulgare.

27. The method of claim 23, wherein said extract of Marrubium vulgare is incorporated in an excipient selected from a cosmetically acceptable excipient and a pharmaceutically acceptable excipient to constitute a composition, to a concentration of an extract of Marrubium vulgare ranging between 0.001% and 5% by weight, based on the total weight of the composition.

28. The method of claim 23, wherein said extract of Marrubium vulgare is an extract of the aerial parts of Marrubium vulgare.

29. The method of claim 22, wherein said extract of Marrubium vulgare is an organic extract of the plant Marrubium vulgare comprising the aerial parts, obtained by a process comprising at least one extraction step with a solvent selected from the group consisting of water, alcohols from 1 to 4 carbon atoms, an aqueous-alcoholic mixture of one of at least one of these alcohols, chlorinated solvents containing one or two carbon atoms, and organic esters from 3 to 6 carbon atoms.

30. The method of claim 22, wherein the extract of Marrubium vulgare is an organic extract of Marrubium vulgare comprising the aerial parts obtained by a process comprising at least one extraction step with a solvent selected from the group consisting of methanol and ethyl acetate.

31. The method of claim 23, wherein said extract of Marrubium vulgare is an organic extract of the plant Marrubium vulgare comprising the aerial parts, obtained by a process comprising at least one extraction step with a solvent selected from the group consisting of water, alcohols from 1 to 4 carbon atoms, an aqeous-alcoholic mixture of one of at least one of these alcohols, chlorinated solvents containing one or two carbon atoms, and organic esters from 3 to 6 carbon atoms.

32. The method of claim 23, wherein the extract of Marrubium vulgare is an organic extract of Marrubium vulgare comprising the aerial parts obtained by a process comprising at least one extraction step with a solvent selected from the group consisting of methanol and ethyl acetate.

33. A method of using an extract of Marrubium vulgare to promote melanin biosynthesis in melanocytes in the scalp or skin of a human being, comprising topically applying to said areas a melanogenesis-stimulating extract of Marrubium vulgare obtained by extraction with a polar solvent in an amount effective to promote melanin biosynthesis in melanocytes.

34. A method of treating a pigmentation insufficiency or pigmentating disorder on given areas of the scalp or skin of a human being, comprising topically applying to said areas a melanogenesis-stimulating extract of Marrubium vulgare obtained by extraction with a polar solvent in an amount effective to promote melanin biosynthesis in melanocytes to restore natural pigmentation of the skin or hair.

35. A method of promoting natural pigmentation of given areas of the skin or hair of a human being, comprising topically applying to said areas a melanogenesis-stimulating extract of Marrubium vulgare obtained by extraction with a polar solvent in an amount effective to promote melanin biosynthesis in melanocytes.

* * * * *